(12) United States Patent
Chareonpanich et al.

(10) Patent No.: US 12,290,801 B2
(45) Date of Patent: May 6, 2025

(54) CATALYST FOR AROMATIZATION OF ALKANES HAVING 4 TO 7 CARBON ATOMS, PROCESS OF MAKING, AND PROCESS OF AROMATICS PREPARATION BY USING THEREOF

(71) Applicant: PTT GLOBAL CHEMICAL PUBLIC COMPANY LIMITED, Bangkok (TH)

(72) Inventors: Metta Chareonpanich, Muang Nonthaburi (TH); Waleeporn Donphai, Muang Samutsakhon (TH); Pariyawalee Sangteantong, Mueang Prachuap Khiri Khan (TH); Yutthana Wongnongwa, Ubon Ratchathani (TH); Siriporn Jungsuttiwong, Ubon Ratchathani (TH); Sitthiphong Pengpanich, Bangkok (TH); Kaew-Arpha Thavornprasert, Bangkok (TH)

(73) Assignee: PTT GLOBAL CHEMICAL PUBLIC COMPANY LIMITED, Bangkok (TH)

( * ) Notice: Subject to any disclaimer, the term of this patent is extended or adjusted under 35 U.S.C. 154(b) by 10 days.

(21) Appl. No.: 18/547,178

(22) PCT Filed: Sep. 23, 2021

(86) PCT No.: PCT/TH2021/000055
§ 371 (c)(1),
(2) Date: Aug. 21, 2023

(87) PCT Pub. No.: WO2022/182301
PCT Pub. Date: Sep. 1, 2022

(65) Prior Publication Data
US 2024/0131503 A1   Apr. 25, 2024
US 2024/0226868 A9   Jul. 11, 2024

(30) Foreign Application Priority Data

Feb. 25, 2021 (TH) ............................... 2101001110

(51) Int. Cl.
*B01J 37/02* (2006.01)
*B01J 23/08* (2006.01)
(Continued)

(52) U.S. Cl.
CPC ........... *B01J 37/0244* (2013.01); *B01J 23/08* (2013.01); *B01J 23/62* (2013.01); *B01J 29/44* (2013.01);
(Continued)

(58) Field of Classification Search
None
See application file for complete search history.

(56) References Cited

U.S. PATENT DOCUMENTS

| 8,772,563 B2 | 7/2014 | Lauritzen et al. |
| 2015/0073450 A1 | 3/2015 | Uchida et al. |
| 2019/0262812 A1 | 8/2019 | Pengpanich |

OTHER PUBLICATIONS

Annex to the International Preliminary Report on Patentability (Chapter II), from PCT/TH21/000055 (Year: 2024).*

(Continued)

*Primary Examiner* — Colin W. Slifka
(74) *Attorney, Agent, or Firm* — Oblon, McClelland, Maier & Neustadt, L.L.P.

(57) ABSTRACT

The present invention relates to a catalyst for aromatization of alkanes having 4 to 7 carbon atoms, especially alkanes having carbon atoms. Said catalyst has the efficacy in the aromatics production with high conversion and high selectivity of aromatics or high yield of aromatics, wherein said catalyst comprises zeolite, at least 1 transition metal from group VIII transition metal in a range of 0.1 to 2% by weight based on the total weight of the catalyst, and at least 1 metal
(Continued)

from group IIIA metal in a range of 0.1 to 5% by weight based on the total weight of the catalyst. Said catalyst is treated and dried with a microwave at a power in a range from 400 to 1,000 watts after step of contacting with a solution comprising at least 1 transition metal salt from group VIII transition metal and after step of contacting with a solution comprising at least 1 group IIIA metal salt. Moreover, this invention also relates to a process for preparing said catalyst and a process of aromatics preparation using said catalyst.

42 Claims, 3 Drawing Sheets

(51) Int. Cl.
| | |
|---|---|
| *B01J 23/62* | (2006.01) |
| *B01J 29/44* | (2006.01) |
| *B01J 37/08* | (2006.01) |
| *B01J 37/34* | (2006.01) |
| *C07C 5/41* | (2006.01) |

(52) U.S. Cl.
CPC ........... *B01J 37/0236* (2013.01); *B01J 37/08* (2013.01); *B01J 37/346* (2013.01); *C07C 5/417* (2013.01); *B01J 2229/20* (2013.01); *C07C 2523/62* (2013.01)

(56) References Cited

OTHER PUBLICATIONS

International Preliminary Report on Patentability issued Feb. 22, 2024 in PCT/TH2021/000055, 5 pages.
International Search Report issued Dec. 27, 2021 in PCT/TH2021/000055, filed on Sep. 23, 2021, 3 pages.
Pentsak et al. "Systematic Study of the Behavior of Different Metal and Metal-Containing Particles under the Microwave Irradiation and Transformation of Nanoscale and Microscale Morphology", Nanomaterials 2019, 9, 19; doi: 10.3390/nano9010019, 18 pages.

* cited by examiner

CATALYST FOR AROMATIZATION OF ALKANES HAVING 4 TO 7 CARBON ATOMS, PROCESS OF MAKING, AND PROCESS OF AROMATICS PREPARATION BY USING THEREOF

CROSS-REFERENCE TO RELATED APPLICATIONS

The present application is a 35 U.S.C. § 371 national stage patent application of International patent application PCT/TH2021/000055, filed on Sep. 23, 2021, which is based on and claims the benefits of priority to Application TH2101001110, filed on Feb. 25, 2021. The entire contents of all of the above applications are incorporated herein by reference.

TECHNICAL FIELD

The present invention relates to the field of chemistry, in particular, to a catalyst for aromatization of alkanes having 4 to 7 carbon atoms, process of making, and process of aromatics preparation by using thereof.

BACKGROUND ART

Aromatics, i.e., benzene, toluene, and xylene are important intermediates in petrochemical industry. They are reactant used for the production of chemicals such as styrene, polyester fiber, nylon 6,6, phenol, terephthalic acid, and especially p-xylene which is one of isomers of xylene that is highly valuable and very important because it is used as the reactant in the production of terephthalic acid for further production of polyester.

Generally, aromatics are produced by dehydrocyclization comprising dehydrogenation and cyclization. The aromatics can be produced from reactant that is heavy naphtha, which is hydrocarbons having 6-12 carbon atoms (C6-C12 hydrocarbons), or light naphtha, which is hydrocarbons having lower carbon atom, i.e., 4-7 carbon atoms (C4-C7 hydrocarbons). However, the process for producing aromatics from both naphtha substances has different difficulty. The aromatics produced from reforming process of heavy naphtha, especially hydrocarbons having 6 carbon atoms, normally is directly occurred via dehydrocyclization using platinum catalyst supported on alumina containing chlorine (Pt/Cl—Al$_2$O$_3$). Meanwhile, the production process of aromatics from light naphtha, especially hydrocarbons having 3-4 carbon atoms or LPG, not only produces aromatics from light naphtha via dehydrocyclization comprising dehydrogenation and cyclization but also needs dimerization because the aromatics products always have the amount of carbon atoms per molecule more than reactants having 2-5 carbon atoms. Therefore, the aromatics production via these reactions are called dehydrocyclodimerization.

However, in the case that the reactant is the light naphtha which is hydrocarbons having 5 carbon atoms, the production mechanism of aromatics is found to be more difficult than the use of heavy naphtha which is hydrocarbons having 6 carbon atoms or light naphtha which is hydrocarbons having 3-4 carbon atoms as reactant. This is because in the production of aromatics, light naphtha which is hydrocarbons having 5 carbon atoms must occur cracking before the formation of aromatics via dehydrocyclization comprising dehydrogenation and cyclization. Further, dimerization is needed before occurring said cyclization, likewise the case of light naphtha which is hydrocarbons having 3-4 carbon atoms.

The documents disclosed about the development and modification of the catalyst performance for the production process of aromatics are as follows:

Patent document No. U.S. Pat. No. 4,304,686A discloses the process for producing aromatics from light naphtha which was hydrocarbons having 3-4 carbon atoms using zeolite catalyst modified with gallium. Said catalyst was active in hydrocarbon conversion reaction such as dehydrocyclodimerization. This work discloses the efficacy testing of said catalyst in dehydrocyclodimerization from the reactant which was the mixture of n-butane, isobutane, propane, and but-2-ene. Similarly, patent document No. U.S. Pat. No. 4,861,933A discloses the process for preparing aromatics from reactant having more than 3 carbon atoms, in which said reactant comprised at least 50% by weight of aliphatic hydrocarbons having 3-12 carbon atoms based on the weight of said reactant, using zeolite catalyst having silica to alumina ratio in the range of 25:1 to 1000:1 and having modification with gallium and calcinated at the temperature of at least 700° C. It was found that when testing in the reactant mostly comprising paraffins having 6-7 carbon atoms, said catalyst calcinated at the temperature of at least 700° C. gave conversion of at least 80% and slightly higher selectivity of benzene, toluene, and xylene (BTX) mixture in the range of 50-56% comparing to the zeolite catalyst modified with gallium and calcinated at the temperature of at least 500° C. which also gave high conversion but provided slightly lower selectivity of benzene, toluene, and xylene (BTX) mixture which was about 47-49%.

However, the use of zeolite catalyst modified with gallium has problem in term of catalyst stability dropped because of the coke formation during the reaction which deteriorate the catalyst. Therefore, in order to overcome said problem, there is the catalyst modification by addition of the second metal in order to improve the catalyst efficacy and reduce the coke formation on the catalyst. The modification of catalyst efficacy by addition of the second metal has been disclosed in the following prior art.

Patent document No. U.S. Pat. No. 4,654,455A discloses the process for producing aromatics from aliphatic hydrocarbons having 2-5 carbon atoms via dehydrocyclodimerization using catalyst comprising alumina having phosphorous, gallium, and zeolite having silica to alumina ratio of at least 12. It was found that when testing the production of aromatics from hydrocarbons having 4 carbon atoms, the phosphorous addition in the amount of 11% by weight into zeolite catalyst having gallium could reduce coke formation for 5 times, but the selectivity of aromatics increased slightly and the conversion still remained comparing to the zeolite catalyst having only gallium.

Patent document No. U.S. Pat. No. 5,192,728A discloses the efficacy testing result of the platinum catalyst supported on the zeolite support having gallium (Pt/Ga-ZSM 5) in the aromatization of n-hexane and heptane. It was found that said catalyst would promote the cracking of reactant to main product which is a large amount of hydrocarbons having 3-4 carbon atoms, whereas the selectivity of aromatics and yield of aromatics were rather very low. The total yield of benzene and toluene was less than 20%. When using platinum catalyst supported on zeolite support having titanium (Pt/TiZSM 5) in the aromatization of n-heptane, it was found that said catalyst gave high conversion and gave selectivity and yield of toluene of about 30%.

Patent document No. U.S. Pat. No. 7,186,872B2 discloses the process for producing aromatics from alkanes having 2-6 carbon atoms using catalyst comprising zeolite, gallium, and platinum. It was found that when testing the production of aromatics from pure propane reactant, the platinum catalyst supported on zeolite having gallium in its structure (Pt/Ga-ZSM 5) gave the selectivity of benzene, toluene, and xylene (BTX) mixture of about 40-50% and the conversion of about 20-30%. Meanwhile, the zeolite catalyst impregnated with gallium and platinum subsequently (Pt/Ga/ZSM-5) gave the selectivity of benzene, toluene, and xylene (BTX) mixture of about 30% and the conversion of about 50-60%. The platinum catalyst supported on zeolite (Pt/ZSM-5) gave selectivity of benzene, toluene, and xylene (BTX) mixture of about 35-45% and conversion of about 50-55%. From the comparison testing result disclosed in said work, it could be seen that the catalyst having same compositions would not provide the same catalyst efficacy. The different efficacies disclosed in this document might be occurred due to the different preparation processes which caused the different catalyst characteristics. Therefore, it was found that the platinum addition onto zeolite catalyst having gallium in its structure gave different results from the platinum addition onto zeolite impregnated with gallium. The platinum addition onto zeolite catalyst having gallium in its structure provided better selectivity of benzene, toluene, and xylene (BTX) mixture, but the platinum addition onto zeolite catalyst impregnated with gallium gave better conversion.

Therefore, after consideration it could be seen that the catalyst composition comprising zeolite, gallium, and platinum is interesting to be further studied and developed in order to improve the efficacy for the aromatics production process of said catalyst to be better than ever. That is to provide higher conversion along with higher selectivity of aromatics. Moreover, it could be noticed that both patent documents No. U.S. Pat. Nos. 5,192,728A and 7,186,872B2 disclose the catalyst having same said compositions, but both documents do not clearly disclose the catalyst efficacy in the production of aromatics from alkanes having 5 carbon atoms. From said above, the mechanism of aromatics production from alkanes having 5 carbon atoms is more complicated and difficult than alkanes having 3-4 carbon atoms or 6 carbon atoms.

For the application of using the microwave as heat source, it is found that there is using the microwave to apply in the step of catalyst preparation process or the aromatics production process. The examples of the application of using the microwave are shown as follows:

Research document of Suitao Qi et al. (Catalysis Today, 2004, 98, 639-645) discloses the application of using the microwave for heating in the process for preparing molybdenum catalyst supported on HZSM-5 zeolite (Mo/HZSM-5) or molybdenum with copper supported on HZSM-5 zeolite (Cu—Mo/HZSM-5). It was found that when testing the aromatization of methane, said catalyst prepared by microwave heating gave higher benzene selectivity than the catalyst prepared by conventional heating. Moreover, it was found that the carbonaceous deposition on the catalyst prepared by microwave heating was less than the catalyst prepared by conventional heating.

Research document of J Gui et al. (Petroleum Science and Technology, 2008, 26, 506-513) discloses the application of using the microwave for heating in during the aromatics production via aromatization of n-hexane by HZSM-5 zeolite catalyst and zinc with nickel supported on HZSM-5 zeolite comparing to the conventional heating in the aromatics production. It was found that the yield of aromatics and benzene, toluene, and xylene (BTX) mixture of the aromatics production process using microwave heating application was higher than conventional heating in the aromatics production.

Patent document No. CN104817095A discloses the application of using the microwave together with adjusting the mole ratio of zinc to aluminum (Zn/Al) in the preparation of zinc catalyst supported on MFI molecular sieve having aluminum (Zn/Al-MFI molecular sieve) by microwave heating for 10-30 minutes in the step of crystal preparation. This work discloses that said catalyst having controlled mole ratio of zinc to aluminum gave improved selectivity in aromatization, lower carbonaceous deposition, and improved catalyst stability. Nevertheless, this work does not show clearly result of the number of conversion, selectivity, or yield of aromatics.

Patent document No. CN1128123C discloses the application of using the microwave in the treatment of molybdenum catalyst supported on HZSM-5 zeolite (Mo/HZSM-5) for the aromatics production from methane via oxygen-free dehydrogenating aromatization. This work discloses the use of microwave as the heat source in the catalyst preparation process by treating the catalyst obtained after mixing step of molybdenum oxide and zeolite at the power of 100-200 watts/g and frequency of 1000-3000 MHz. It was found that the arenes selectivity of the catalyst in this work was improved up to 20% in which the arenes selectivity was 70-85% and the carbonaceous deposition was reduced. However, the number of methane conversion disclosed in this work was still low at about 8-12%. Moreover, although the carbonaceous deposition was reduced, the number of coking selectivity was still high at 10-25%.

Patent document No. CN1176187C discloses the application of using the microwave for heating the zinc and nickel catalyst supported on HZSM-5 zeolite (Zn—Ni/HZSM-5) for the aromatization from hydrocarbons having 2-6 carbon atoms. It was found that when testing the aromatics production from hydrocarbons mostly having 3-4 carbon atoms, the catalyst subjected to microwave drying for 10-15 minutes gave higher yield of benzene, toluene, and xylene (BTX) mixture than the catalyst subjected to conventional drying. The yield of benzene, toluene, and xylene (BTX) mixture of the catalyst subjected to microwave drying, which is disclosed in this work, was about 60% which was slightly higher than the conventional drying (higher for about 4%).

The application of using the microwave in the catalyst preparation step by subjecting catalyst to the microwave treatment is interesting. However, from documents above, it is found that the application of using the microwave by said method gives different results of the catalyst efficacy in the aromatics production process. Some documents disclose the result of arenes selectivity which is clearly improved, but some documents find that the yield of benzene, toluene, and xylene (BTX) mixture is slightly improved only. This difference may be due to the different catalyst systems.

From all reasons above, this invention aims to prepare a catalyst for aromatization of alkanes having 4 to 7 carbon atoms, especially alkanes having 5 carbon atoms, by improving the catalyst efficacy with the addition of other metals and the application of using the microwave in the catalyst treatment during preparation process of said catalyst in order to obtain the efficient catalyst in the aromatics production, wherein said catalyst provides high conversion and high selectivity of aromatics or high yield of aromatics.

SUMMARY OF INVENTION

The present invention aims to prepare a catalyst for aromatization of alkanes having 4 to 7 carbon atoms, especially alkanes having 5 carbon atoms, wherein said catalyst has the efficacy in the aromatics production with high conversion and high selectivity of aromatics or high yield of aromatics.

Said catalyst comprises zeolite, at least 1 transition metal from group VIII transition metal in a range of 0.1 to 2% by weight based on the total weight of the catalyst, and at least 1 metal from group ETA metal in a range of 0.1 to 5% by weight based on the total weight of the catalyst, wherein said catalyst is prepared from a process comprising:
  a) contacting a zeolite with a solution comprising at least 1 transition metal salt from group VIII transition metal;
  b) treating and drying the mixture obtained from step a) with a microwave at a power in a range from 400 to 1,000 watts;
  c) contacting the mixture obtained from step b) with a solution comprising at least 1 group IIIA metal salt;
  d) treating and drying the mixture obtained from step c) with a microwave at a power in a range from 400 to 1,000 watts; and
  e) calcining the mixture obtained from step d) at a temperature less than or equal to 650° C.

DESCRIPTION OF THE INVENTION

The present invention relates to a catalyst for aromatization of alkanes having 4 to 7 carbon atoms, especially alkanes having 5 carbon atoms, wherein said catalyst has the efficacy in the aromatics production with high conversion and high selectivity of aromatics or high yield of aromatics, which will be described according to the following aspects of the invention.

Any aspect being shown herein also means to include the application to other aspects of this invention unless stated otherwise.

Technical terms or scientific terms used herein have definitions as understood by an ordinary person skilled in the art unless stated otherwise.

Any tools, equipment, methods, or chemicals named herein mean tools, equipment, methods, or chemicals being operated or used commonly by those person skilled in the art unless stated otherwise that they are tools, equipment, methods, or chemicals specific only in this invention.

Use of singular noun or singular pronoun with "comprising" in claims or specification means "one" and also including "one or more", "at least one", and "one or more than one" too.

All compositions and/or methods disclosed and claims in this application are intended to cover embodiments from any operation, performance, modification, or adjustment any factors without any experiment that significantly different from this invention, and obtain with object with utility and resulted as same as the present embodiment according to person ordinary skilled in the art although without specifically stated in claims. Therefore, substitutable or similar object to the present embodiment, including any minor modification or adjustment that can be apparent to person skilled in the art should be construed as remains in spirit, scope, and concept of invention as appeared in appended claims.

Throughout this application, term "about" means any number that appeared or expressed herein that could be varied or deviated from any error of equipment, method, or personal using said equipment or method.

The term "zeolite" in this invention means aluminosilicate compound containing silicon, aluminium, and oxygen in its structure, which may be the commercial zeolite or zeolite prepared by any method.

The group name in the periodic table in this invention refers to the group name according to CAS system. For example, the group VIII transition metal is the transition metals in the same group as the transition metals of Nickel group. The group WB transition metal is the transition metals in the same group as the transition metals of Titanium group, and the group IIIA metal is the metals in the same group as the metals of Boron group.

Hereafter, invention embodiments are shown without any purpose to limit any scope of the invention.

This invention relates to a catalyst for aromatization of alkanes having 4 to 7 carbon atoms, especially alkanes having 5 carbon atoms, wherein said catalyst has the efficacy in the aromatics production with high conversion and high selectivity of aromatics or high yield of aromatics. Said catalyst comprises zeolite, at least 1 transition metal from group VIII transition metal in a range of 0.1 to 2% by weight based on the total weight of the catalyst, and at least 1 metal from group IIIA metal in a range of 0.1 to 5% by weight based on the total weight of the catalyst, wherein said catalyst is prepared from a process comprising:
  a) contacting a zeolite with a solution comprising at least 1 transition metal salt from group VIII transition metal;
  b) treating and drying the mixture obtained from step a) with a microwave at a power in a range from 400 to 1,000 watts;
  c) contacting the mixture obtained from step b) with a solution comprising at least 1 group IIIA metal salt;
  d) treating and drying the mixture obtained from step c) with a microwave at a power in a range from 400 to 1,000 watts; and
  e) calcining the mixture obtained from step d) at a temperature less than or equal to 650° C.

In one aspect of the invention, the zeolite may be selected from, but not limited to MFI-group zeolite selected from ZSM-5, ZSM-11, or a mixture thereof, preferably ZSM-5.

In one aspect of the invention, said zeolite has a mole ratio of silica to alumina in a range from 15 or more, preferably the mole ratio of silica to alumina in the range from 15 to 40, most preferably the mole ratio of silica to alumina in the range from 20 to 30.

In one aspect of the invention, the amount of the group VIII transition metal is in the range from 0.1 to 1% by weight based on the total weight of the catalyst. Preferably, the amount of the group VIII transition metal is in the range from 0.5 to 1% by weight based on the total weight of the catalyst.

In one aspect of the invention, the group VIII transition metal is platinum (Pt).

In one aspect of the invention, the amount of the group IIIA metal is in the range from 0.1 to 2% by weight based on the total weight of the catalyst. Preferably, the amount of the group IIIA metal is in the range from 0.5 to 2% by weight based on the total weight of the catalyst, most preferably in the range from 0.5 to 1% by weight based on the total weight of the catalyst.

In one aspect of the invention, the group IIIA metal is gallium (Ga).

In one aspect of the invention, in step a) contacting the zeolite with the solution comprising at least 1 transition metal salt from group VIII transition metal can be performed using impregnation, ion exchange, precipitation, chemical vapor deposition, or sol-gel technique. Preferably, contacting the zeolite with the solution comprising at least 1 transition metal salt from only group VIII transition metal in step a) is performed using impregnation technique.

In one aspect of the invention, at least 1 transition metal salt from group VIII transition metal may be selected from, but not limited to platinum chloride or hexachloroplatinic acid, preferably hexachloroplatinic acid.

In one aspect of the invention, at least 1 transition metal may further comprise the group IVB transition metal.

In one aspect of the invention, at least 1 transition metal further comprises the group IVB transition metal in which the amount of the group IVB transition metal is in the range from 0.1 to 10% by weight based on the total weight of the catalyst. Preferably, the amount of the group IVB transition metal is in the range from 3 to 5% by weight based on the total weight of the catalyst. Most preferably, the amount of the group IVB transition metal is about 3.5% by weight based on the total weight of the catalyst.

In one aspect of the invention, at least 1 transition metal further comprises the group IVB transition metal in which the group IVB transition metal is titanium (Ti).

In one aspect of the invention, in step a) contacting the zeolite with the solution comprising at least 1 transition metal salt from group VIII transition metal, in which said solution in step a) further comprises at least 1 transition metal salt from group IVB transition metal and said step can be performed using impregnation, ion exchange, precipitation, chemical vapor deposition, or sol-gel technique. Preferably, contacting the zeolite with the solution comprising at least 1 transition metal salt from group VIII transition metal and further comprising at least 1 transition metal salt from group IVB transition metal in step a) is performed using sol-gel technique.

In one aspect of the invention, the solution comprising at least 1 transition metal salt from group VIII transition metal and further comprising at least 1 transition metal salt from group WB transition metal, in which group IVB transition metal salt may be selected from, but not limited to titanium isopropoxide, titanium hydroxide, titanium nitrate, or titanium chloride, preferably titanium isopropoxide or titanium chloride, most preferably titanium isopropoxide.

In one aspect of the invention, the solution comprising at least 1 transition metal salt from group VIII transition metal and further comprising at least 1 transition metal salt from group IVB transition metal, in which group VIII transition metal salt is hexachloroplatinic acid and group IVB transition metal salt is titanium isopropoxide or titanium chloride. Most preferably, group VIII transition metal salt is hexachloroplatinic acid and group IVB transition metal salt is titanium isopropoxide.

In one aspect of the invention, contacting the mixture obtained from step b) with the solution comprising at least 1 group IIIA metal salt can be performed using impregnation, ion exchange, precipitation, or chemical vapor deposition technique, preferably impregnation or ion exchange technique, most preferably impregnation technique.

In one aspect of the invention, at least 1 group IIIA metal salt may be selected from, but not limited to gallium nitrate, gallium chloride, gallium bromide, gallium hydroxide, or gallium acetate, preferably gallium nitrate or gallium acetate, most preferably gallium acetate. In one aspect of the invention, step b) and step d) are performed using the microwave at the power in the range from 600 to 900 watts, preferably at the power of 800 watts.

In one aspect of the invention, step e) is performed at the temperature in a range from 200 to 600° C., preferably the temperature in the range from 400 to 600° C., most preferably the temperature in the range from 500 to 600° C.

In one aspect of the invention, the calcination time of step e) is from 3 to 6 hours.

In one aspect of the invention, said catalyst is prepared by the process that may further comprise the drying step by other techniques other than microwave, if necessary. The drying step by other techniques other than microwave may be performed by, but not limited to conventional drying method using oven, drying via natural evaporation, stirred evaporation, vacuum drying, or drying by rotary evaporator, etc.

In one aspect of the invention, said alkanes are the alkanes having 5 carbon atoms, which are pentane.

In one aspect of the invention, the catalyst described above is used for the process of aromatics preparation from aromatization of alkanes having 5 carbon atoms, which are pentane.

In another aspect of the invention, this invention relates to a process of catalyst preparation for aromatization of alkanes having 4 to 7 carbon atoms comprising:
 a) contacting a zeolite with a solution comprising at least 1 transition metal salt from group VIII transition metal, wherein the group VIII transition metal is in a range of 0.1 to 2% by weight based on the total weight of the catalyst;
 b) treating and drying the mixture obtained from step a) with a microwave at a power in a range from 400 to 1,000 watts;
 c) contacting the mixture obtained from step b) with a solution comprising at least 1 group IIIA metal salt, wherein the group ETA metal is in a range of 0.1 to 5% by weight based on the total weight of the catalyst;
 d) treating and drying the mixture obtained from step c) with a microwave at a power in a range from 400 to 1,000 watts; and
 e) calcining the mixture obtained from step d) at a temperature less than or equal to 650° C.

In one aspect of the invention, the amount of the group VIII transition metal is in the range from 0.1 to 1% by weight based on the total weight of the catalyst. Preferably, the amount of the group VIII transition metal is in the range from 0.5 to 1% by weight based on the total weight of the catalyst.

In one aspect of the invention, the group VIII transition metal is platinum (Pt).

In one aspect of the invention, the amount of the group IIIA metal is in the range from 0.1 to 2% by weight based on the total weight of the catalyst. Preferably, the amount of the group IIIA metal is in the range from 0.5 to 2% by weight based on the total weight of the catalyst, most preferably in the range from 0.5 to 1% by weight based on the total weight of the catalyst.

In one aspect of the invention, the group IIIA metal is gallium (Ga).

In one aspect of the invention, in step a) contacting the zeolite with the solution comprising at least 1 transition metal salt from group VIII transition metal can be performed using impregnation, ion exchange, precipitation, chemical vapor deposition, or sol-gel technique. Preferably, contacting the zeolite with the solution comprising at least 1 transition metal salt from only group VIII transition metal in step a) is performed using impregnation technique.

In one aspect of the invention, at least 1 transition metal salt from group VIII transition metal may be selected from, but not limited to platinum chloride or hexachloroplatinic acid, preferably hexachloroplatinic acid.

In one aspect of the invention, the solution comprising at least 1 transition metal salt in step a) may further comprise at least 1 transition metal salt from group IVB transition metal.

In one aspect of the invention, the solution comprising at least 1 transition metal salt in step a) further comprises at least 1 transition metal salt from group IVB transition metal in which the amount of the group IVB transition metal is in the range from 0.1 to 10% by weight based on the total weight of the catalyst. Preferably, the amount of the group WB transition metal is in the range from 3 to 5% by weight based on the total weight of the catalyst. Most preferably, the amount of the group IVB transition metal is about 3.5% by weight based on the total weight of the catalyst.

In one aspect of the invention, the solution comprising at least 1 transition metal salt in step a) further comprises at least 1 transition metal salt from group IVB transition metal in which the group IVB transition metal is titanium (Ti).

In one aspect of the invention, in step a) contacting the zeolite with the solution comprising at least 1 transition metal salt from group VIII transition metal, in which said solution in step a) further comprises at least 1 transition metal salt from group WB transition metal and said step can be performed using impregnation, ion exchange, precipitation, chemical vapor deposition, or sol-gel technique. Preferably, contacting the zeolite with the solution comprising at least 1 transition metal salt from group VIII transition metal and further comprising at least 1 transition metal salt from group IVB transition metal in step a) is performed using sol-gel technique.

In one aspect of the invention, the solution comprising at least 1 transition metal salt in step a) further comprises at least 1 transition metal salt from group IVB transition metal, in which group IVB transition metal salt may be selected from, but not limited to titanium isopropoxide, titanium hydroxide, titanium nitrate, or titanium chloride, preferably titanium isopropoxide or titanium chloride, most preferably titanium isopropoxide.

In one aspect of the invention, the solution comprising at least 1 transition metal salt from group VIII transition metal and further comprising at least 1 transition metal salt from group IVB transition metal, in which group VIII transition metal salt is hexachloroplatinic acid and group IVB transition metal salt is titanium isopropoxide or titanium chloride. Most preferably, group VIII transition metal salt is hexachloroplatinic acid and group WB transition metal salt is titanium isopropoxide.

In one aspect of the invention, contacting the mixture obtained from step b) with the solution comprising at least 1 group IIIA metal salt can be performed using impregnation, ion exchange, precipitation, or chemical vapor deposition technique, preferably impregnation or ion exchange technique, most preferably impregnation technique.

In one aspect of the invention, at least 1 group IIIA metal salt may be selected from, but not limited to gallium nitrate, gallium chloride, gallium bromide, gallium hydroxide, or gallium acetate, preferably gallium nitrate or gallium acetate, most preferably gallium acetate. In one aspect of the invention, the zeolite in step a) may be selected from, but not limited to MFI-group zeolite selected from ZSM-5, ZSM-11, or a mixture thereof, preferably ZSM-5. In one aspect of the invention, the zeolite in step a) has a mole ratio of silica to alumina in a range from 15 or more, preferably the mole ratio of silica to alumina in the range from 15 to 40, most preferably the mole ratio of silica to alumina in the range from 20 to 30.

In one aspect of the invention, step b) and step d) are performed using the microwave at the power in the range from 600 to 900 watts, preferably at the power of 800 watts.

In one aspect of the invention, step e) is performed at the temperature in the range from 200 to 600° C., preferably the temperature in the range from 400 to 600° C., most preferably the temperature in the range from 500 to 600° C.

In one aspect of the invention, the calcination time of step e) is from 3 to 6 hours.

In one aspect of the invention, said process of catalyst preparation may further comprise the drying step by other techniques other than microwave, if necessary. The drying step by other techniques other than microwave may be performed by, but not limited to conventional drying method using oven, drying via natural evaporation, stirred evaporation, vacuum drying, or drying by rotary evaporator, etc.

In one aspect of the invention, said alkanes are the alkanes having 5 carbon atoms, which are pentane.

In one aspect of the invention, the catalyst obtained from process of catalyst preparation described above is used for the process of aromatics preparation from aromatization of alkanes having 5 carbon atoms, which are pentane.

In another aspect of the invention, this invention relates to a process of aromatics preparation, especially benzene, toluene, and xylene (BTX), from aromatization of alkanes using the catalyst according to the invention or the catalyst obtained from process of catalyst preparation according to the invention, comprising:
 a) treating the catalyst according to the invention or the catalyst obtained from process of catalyst preparation according to the invention with gas comprising hydrogen gas at a temperature in a range from 200 to 650° C.; and
 b) contacting alkanes with the catalyst obtained from step a) at the temperature in the range from 400 to 800° C.

In one aspect of the invention, step a) is performed at the temperature in the range from 400 to 600° C.

In one aspect of the invention, step b) is performed at the temperature in the range from 500 to 600° C.

In one aspect of the invention, alkanes for said process of aromatics preparation from aromatization are selected from alkanes having 4 to 7 carbon atoms, preferably alkanes having 5 carbon atoms which are pentane.

In one aspect of the invention, the weight hourly space velocity (WHSV) for the alkane feed line in aromatization is in a range between about 1 to 30 hour$^{-1}$, preferably in the range about 2 to 10 hour$^{-1}$.

In one aspect, the process of aromatics preparation from aromatization of alkanes may be performed in the reactor, but not limited to the fixed-bed reactor which may be performed in batch or continuous manner, or may be performed in fixed bed system, moving bed system, fluidized bed system, or batch system.

Generally, any persons skilled in this art can adjust the aromatization conditions to be suitable for type and composition of feed line, catalyst, and reactor system.

The following examples are for demonstrating one aspect of this invention only, not for limiting the scope of this invention in any way.

Preparation of the Catalyst

The preparation of the catalyst comprising zeolite, at least 1 transition metal from group VIII transition metal in a range of 0.1 to 2% by weight based on the total weight of the catalyst, and at least 1 metal from group IIIA metal in a range of 0.1 to 5% by weight based on the total weight of the catalyst, wherein said catalyst may be prepared from a process comprising:

a) contacting a zeolite with a solution comprising at least 1 transition metal salt from group VIII transition metal;
b) treating and drying the mixture obtained from step a) with a microwave at a power in a range from 400 to 1,000 watts;
c) contacting the mixture obtained from step b) with a solution comprising at least 1 group IIIA metal salt;
d) treating and drying the mixture obtained from step c) with a microwave at a power in a range from 400 to 1,000 watts; and
e) calcining the mixture obtained from step d) at a temperature less than or equal to 650° C.

The details of the step for the contacting of the solution comprising at least 1 transition metal salt in step a), the step for the contacting of the solution comprising group IIIA metal salt in step c), and the step for the calcination in step e) can be described as follows:

Contacting a Zeolite with a Solution Comprising Group VIII Transition Metal Salt The solution comprising group VIII transition metal salt, which was hexachloroplatinic acid, was prepared using the amount in which the amount of group VIII transition metal was in the range of 0.1 to 2% by weight based on the total weight of the catalyst. The 30 milliliters of distilled water was added and the mixture obtained was stirred and heated at the temperature of 80° C. for 30 minutes. After that, 2 g of ZSM-5 zeolite having a mole ratio of silica to alumina of about 23 to 25 was added into said solution. Then, said mixture was further stirred at the temperature of 80° C. for 60 minutes.

Contacting a Zeolite with a Solution Comprising Group VIII Transition Metal Salt and Group IVB Transition Metal Salt The solution comprising group VIII transition metal salt and group WB transition metal salt was prepared by adding group WB transition metal salt, which was titanium isopropoxide, in the amount in which the amount of group IVB transition metal was in a range from 0.1 to 10% by weight based on the total weight of the catalyst into 30 mL of 28% concentrated ammonium hydroxide solution. The mixture obtained was stirred and heated at the temperature of 80° C. for 30 minutes. Then, the group VIII transition metal salt, which was hexachloroplatinic acid, in the amount in which the amount of group VIII transition metal was in the range of 0.1 to 2% by weight based on the total weight of the catalyst was added into said solution. After that, 2 g of ZSM-5 zeolite having the mole ratio of silica to alumina of about 23 to 25 was added into said solution. Then, said mixture was further stirred at the temperature of 80° C. until the gel substance was obtained.

Contacting with a Solution Comprising Group IIIA Metal Salt

The mixture obtained from step b) was contacted with the solution comprising group IIIA metal salt, which was gallium acetate, by impregnation technique operated at room temperature. The amount of group IIIA metal was in the range of 0.1 to 5% by weight based on the total weight of the catalyst.

Calcination of the Mixture

The calcination of the mixture obtained from step d) was operated at the temperature of 550° C. for 5 hours with heating rate of 10° C./min.

Example of a Preparation of Catalyst According to the Invention and a Preparation of Comparative Catalyst Example of a Comparative Catalyst Cat A The comparative catalyst Cat A was prepared from the process described above wherein step a) was the contacting of zeolite with the solution comprising group VIII transition metal salt using about 0.03 g of hexachloroplatinic acid, step b) treating and drying the mixture obtained from step a) with the microwave was changed to drying the mixture obtained from step a) at the temperature of 110° C. overnight, and step d) treating and drying the mixture obtained from step c) with the microwave was changed to drying the mixture obtained from step c) at the temperature of 110° C. overnight.

The comparative catalyst Cat A had about 1% by weight of platinum (Pt) and about 1% by weight of gallium (Ga) based on the total weight of the catalyst.

Example of a Comparative Catalyst Cat B

The comparative catalyst Cat B was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, step b) treating and drying the mixture obtained from step a) with the microwave was changed to drying the mixture obtained from step a) at the temperature of 110° C. overnight, and step d) treating and drying the mixture obtained from step c) with the microwave was changed to drying the mixture obtained from step c) at the temperature of 110° C. overnight.

The comparative catalyst Cat B had about 3.5% by weight of titanium (Ti), about 1% by weight of platinum (Pt), and about 1% by weight of gallium (Ga) based on the total weight of the catalyst.

Example of a Comparative Catalyst Cat C

The comparative catalyst Cat C was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, step b) treating and drying the mixture obtained from step a) with the microwave was changed to drying the mixture obtained from step a) at the temperature of 110° C. overnight, and in step d) the mixture obtained from step c) was treated and dried with the microwave at the power of 800 watts until dry.

The comparative catalyst Cat C had about 3.5% by weight of titanium (Ti), about 1% by weight of platinum (Pt), and about 1% by weight of gallium (Ga) based on the total weight of the catalyst.

Example of a Comparative Catalyst Cat D

The comparative catalyst Cat D was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, in step b) the mixture obtained from step a) was treated and dried with the microwave at the power of 800 watts until dry, and step d) treating and drying the mixture obtained from step c) with the microwave was changed to drying the mixture obtained from step c) at the temperature of 110° C. overnight.

The comparative catalyst Cat D had about 3.5% by weight of titanium (Ti), about 1% by weight of platinum (Pt), and about 1% by weight of gallium (Ga) based on the total weight of the catalyst.

Example of a Catalyst According to the Invention Cat 1

The catalyst according to the invention Cat 1 was prepared from the process described above wherein step a) was the contacting of zeolite with the solution comprising group VIII transition metal salt using about 0.03 g of hexachloroplatinic acid and in step b) and step d) the mixture was treated and dried with the microwave at the power of 800 watts until dry. The catalyst according to the invention Cat 1 had about 1% by weight of platinum (Pt) and about 1% by weight of gallium (Ga) based on the total weight of the catalyst.

Example of a Catalyst According to the Invention Cat 2

The catalyst according to the invention Cat 2 was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, and in step b) and step d) the mixture was treated and dried with the microwave at the power of 800 watts until dry.

The catalyst according to the invention Cat 2 had about 3.5% by weight of titanium (Ti), about 1% by weight of platinum (Pt), and about 1% by weight of gallium (Ga) based on the total weight of the catalyst.

Example of a Catalyst According to the Invention Cat 3

The catalyst according to the invention Cat 3 was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, and in step b) and step d) the mixture was treated and dried with the microwave at the power of 400 watts until dry.

The catalyst according to the invention Cat 3 had about 3.5% by weight of titanium (Ti), about 1% by weight of platinum (Pt), and about 1% by weight of gallium (Ga) based on the total weight of the catalyst.

Example of a Catalyst According to the Invention Cat 4

The catalyst according to the invention Cat 4 was prepared from the process described above wherein step a) was the contacting of zeolite with the solution comprising group VIII transition metal salt and group IVB transition metal salt using about 0.423 g and 0.03 g of titanium isopropoxide and hexachloroplatinic acid respectively, and in step b) and step d) the mixture was treated and dried with the microwave at the power of 1000 watts until dry.

The catalyst according to the invention Cat 4 had about 3.5% by weight of titanium (Ti), about 1% by weight of platinum (Pt), and about 1% by weight of gallium (Ga) based on the total weight of the catalyst.

Example of a Catalyst According to the Invention Cat 5

The catalyst according to the invention Cat 5 was prepared from the process described above wherein step a) was the contacting of zeolite with the solution comprising group VIII transition metal salt and group IVB transition metal salt using about 0.338 g and 0.03 g of titanium isopropoxide and hexachloroplatinic acid respectively, and in step b) and step d) the mixture was treated and dried with the microwave at the power of 800 watts until dry.

The catalyst according to the invention Cat 5 had about 3% by weight of titanium (Ti), about 1% by weight of platinum (Pt), and about 1% by weight of gallium (Ga) based on the total weight of the catalyst.

Example of a Catalyst According to the Invention Cat 6

The catalyst according to the invention Cat 6 was prepared from the process described above wherein step a) was the contacting of zeolite with the solution comprising group VIII transition metal salt and group IVB transition metal salt using about 0.508 g and 0.03 g of titanium isopropoxide and hexachloroplatinic acid respectively, and in step b) and step d) the mixture was treated and dried with the microwave at the power of 800 watts until dry.

The catalyst according to the invention Cat 6 had about 5% by weight of titanium (Ti), about 1% by weight of platinum (Pt), and about 1% by weight of gallium (Ga) based on the total weight of the catalyst.

Example of a Catalyst According to the Invention Cat 7

The catalyst according to the invention Cat 7 was prepared from the process described above wherein step a) was the contacting of zeolite with the solution comprising group VIII transition metal salt and group IVB transition metal salt using about 0.423 g and 0.003 g of titanium isopropoxide and hexachloroplatinic acid respectively, and in step b) and step d) the mixture was treated and dried with the microwave at the power of 800 watts until dry.

The catalyst according to the invention Cat 7 had about 3.5% by weight of titanium (Ti), about 0.1% by weight of platinum (Pt), and about 1% by weight of gallium (Ga) based on the total weight of the catalyst.

Example of a Catalyst According to the Invention Cat 8

The catalyst according to the invention Cat 8 was prepared from the process described above wherein step a) was the contacting of zeolite with the solution comprising group VIII transition metal salt and group IVB transition metal salt using about 0.423 g and 0.015 g of titanium isopropoxide and hexachloroplatinic acid respectively, and in step b) and step d) the mixture was treated and dried with the microwave at the power of 800 watts until dry.

The catalyst according to the invention Cat 8 had about 3.5% by weight of titanium (Ti), about 0.5% by weight of platinum (Pt), and about 1% by weight of gallium (Ga) based on the total weight of the catalyst.

Testing of a Process of Aromatics Preparation from Aromatization Reaction

The testing for the efficacy of the catalyst in the process of aromatics preparation from aromatization reaction of alkanes might be performed as follows:
   a) The pretreatment of the catalyst with hydrogen gas at the flow rate of about 50 mL/min was performed, wherein this pretreatment was performed at the temperature of about 500° C. for about 1 hour. When the time was reached, the hydrogen gas was changed to nitrogen gas at the flow rate of about 20 mL/min.

b) The contacting of alkanes, which were pentane, with the catalyst in the fixed bed reactor was started by feeding of alkanes with flow control device at the flow rate of about 0.052 mL/min into heated pipe and the temperature was controlled at about 120° C. before entering into the reactor. Reactor's inside was heated by the pipe oven at the temperature of 500° C. Said alkane feed was fed into the reactor containing catalyst with the space velocity of 5 hour$^{-1}$.

c) The chemical composition analysis was performed by subjecting the obtained product to the chemical composition analysis using gas chromatography technique. The conversion of n-pentane and the selectivity of aromatics product could be calculated as follows:

Conversion of $n$-pentane=((weight of starting $n$-pentane−weight of $n$-pentane remained from the reaction)/weight of starting$n$-pentane)×100

Selectivity of aromatics=(weight of generated benzene,toluene, and xylene/weight of total product generated from the reaction)×100

Figure 1:
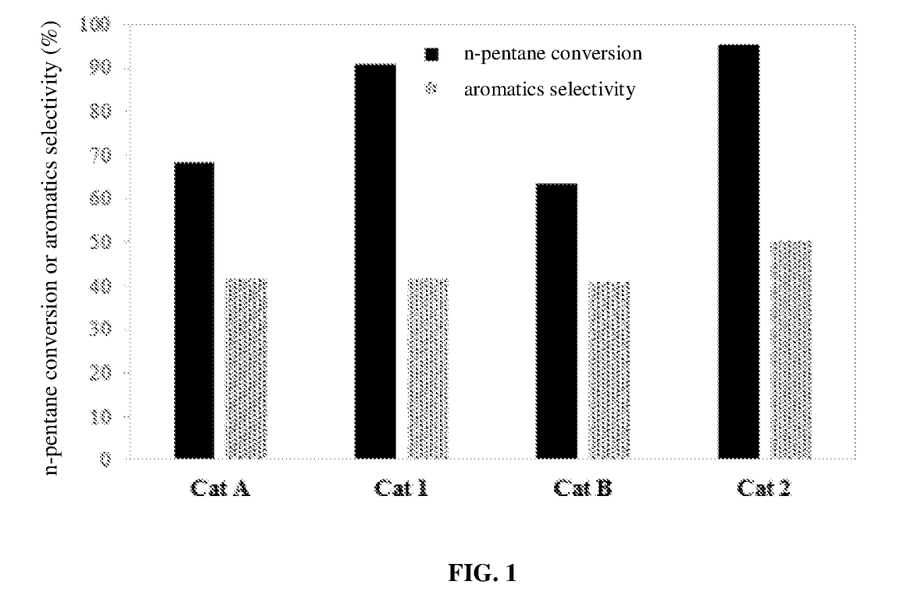
FIG. 1 shows the conversion of n-pentane and selectivity of aromatics of the catalyst modified by treatment and drying with microwave and further modified by addition of the group IVB transition metal comparing to the catalyst subjected to conventional drying.
Figure 2:
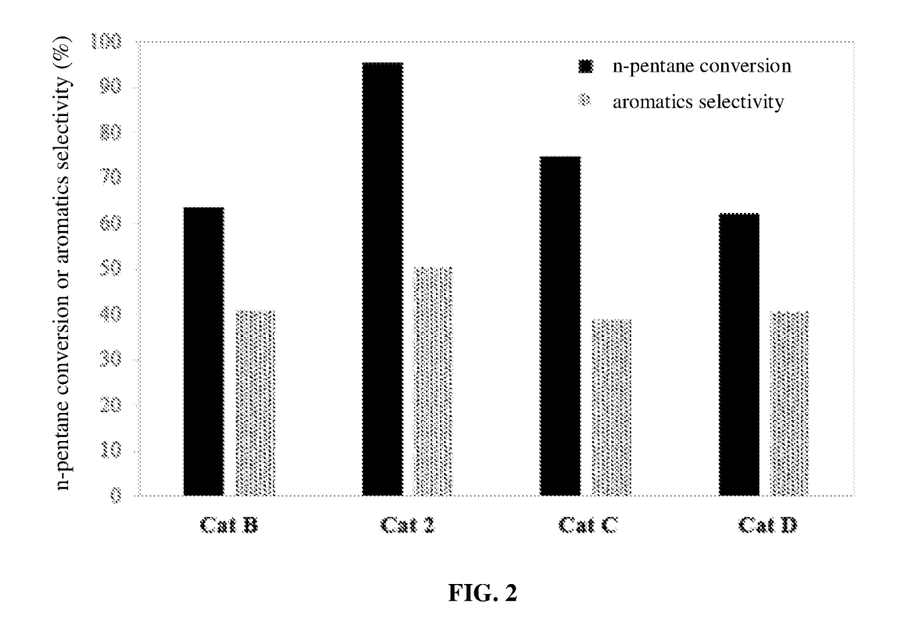
FIG. 2 shows the conversion of n-pentane and selectivity of aromatics of the catalyst modified by addition of the group IVB transition metal and modified by treatment and drying with microwave at different steps comparing to the catalyst subjected to conventional drying.

FIG. 1 shows the results of n-pentane conversion and aromatics selectivity of the catalyst modified by the treatment and drying with microwave and further modified by the addition of the group WB transition metal comparing to the catalyst subjected to conventional drying. It was found that the treatment and drying with microwave improved and increased the efficacy of the catalyst especially the n-pentane conversion which was clearly increased. Moreover, when the catalyst system was further modified by the addition of the group IVB transition metal, the results were found that both n-pentane conversion and aromatics selectivity were clearly increased. When considering the effect of the treatment and drying with microwave at different steps on the catalyst modified by the addition of the group IVB transition metal, the results are shown in FIG. 2 and it was found that the catalyst subjected to the treatment and drying with microwave after both of the metal additions showed highest efficacy for the production of aromatics from aromatization reaction.

Figure 3:
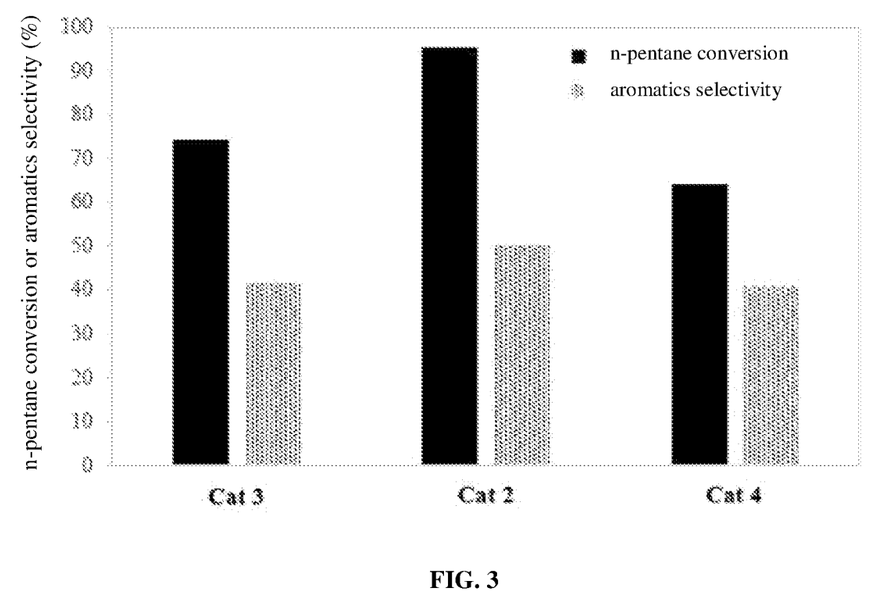
FIG. 3 shows the conversion of n-pentane and selectivity of aromatics of the catalyst modified by addition of the group IVB transition metal and modified by treatment and drying with microwave at different microwave powers.
Figure 4:
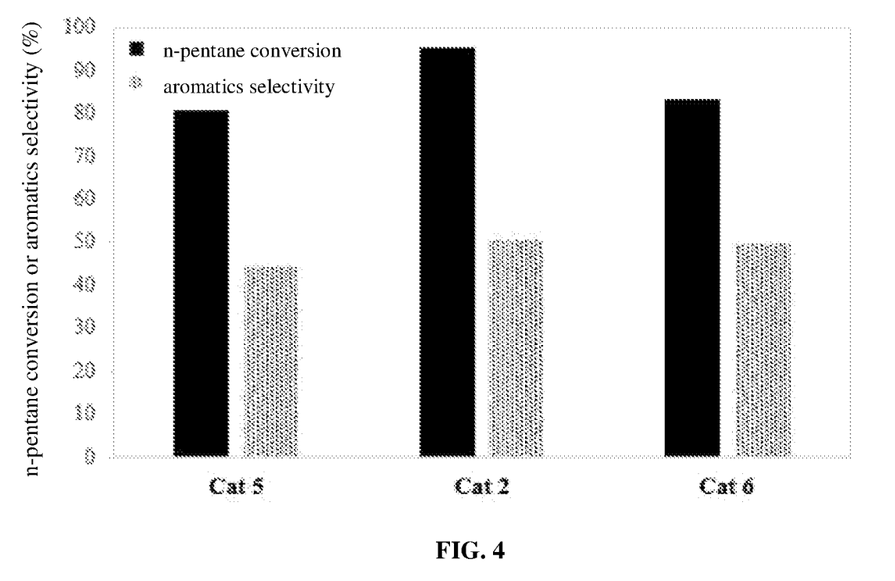
FIG. 4 shows the conversion of n-pentane and selectivity of aromatics of the catalyst modified by treatment and drying with microwave and modified by addition of the group IVB transition metal at different amounts.
Figure 5:
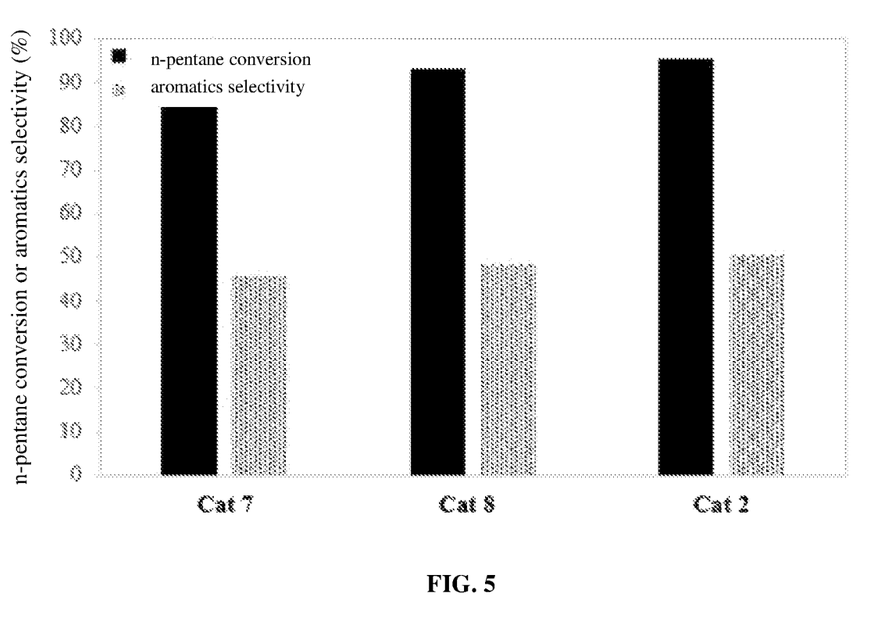
FIG. 5 shows the conversion of n-pentane and selectivity of aromatics of the catalyst modified by treatment and drying with microwave and modified by addition of the group IVB transition metal in which said catalyst contains different amounts of the group VIII transition metal.

When considering the power of microwave being used as shown in FIG. 3, it was found that the power of microwave affected the efficacy of the catalyst in the production of the aromatics. The most suitable power of the microwave which resulted in the highest efficacy of the catalyst was 800 watts. When considering the different amounts of the group IVB transition metal in FIG. 4, it was found that the catalyst, which was modified by the treatment and drying with microwave and had the amount of titanium in the range of 3 to 5% by weight based on the total weight of the catalyst, provided good efficacy for the production of the aromatics in which the n-pentane conversion was not less than 80% similar to the catalyst modified by the treatment and drying with microwave and further modified by the addition of the group WB transition metal in which said catalyst had the amount of platinum in the range of 0.1 to 1% by weight based on the total weight of the catalyst as shown in FIG. 5.

BEST MODE OR PREFERRED EMBODIMENT OF THE INVENTION

Best mode or preferred embodiment of the invention is as provided in the description of the invention.

The invention claimed is:

1. A catalyst for aromatization of alkanes having 4 to 7 carbon atoms comprising zeolite, at least 1 transition metal from group VIII transition metal in a range of 0.1 to 2% by weight based on the total weight of the catalyst, and at least 1 metal from group IIIA metal in a range of 0.1 to 5% by weight based on the total weight of the catalyst, wherein said catalyst is prepared from a process comprising:
    a) contacting a zeolite with a solution comprising at least 1 transition metal salt from group VIII transition metal to form a first mixture;
    b) treating and drying the first mixture obtained from step a) with a microwave at a power in a range from 400 to 1,000 watts to form a first dried mixture;
    c) contacting the first dried mixture obtained from step b) with a solution comprising at least 1 group IIIA metal salt to form a second mixture;
    d) treating and drying the second mixture obtained from step c) with a microwave at a power in a range from 400 to 1,000 watts to form a second dried mixture; and
    e) calcining the second dried mixture obtained from step d) at a temperature less than or equal to 650° C.

2. The catalyst according to claim 1, wherein the zeolite is selected from ZSM-5, ZSM-11, or a mixture thereof.

3. The catalyst according to claim 2, wherein the zeolite is ZSM-5.

4. The catalyst according to claim 1, wherein said zeolite has a mole ratio of silica to alumina in a range from 15 to 40.

5. The catalyst according to claim 4, wherein said zeolite has the mole ratio of silica to alumina in the range from 20 to 30.

6. The catalyst according to claim 1, wherein the amount of the group VIII transition metal is in the range from 0.5 to 1% by weight based on the total weight of the catalyst.

7. The catalyst according to claim 1, wherein the group VIII transition metal is platinum (Pt).

8. The catalyst according to claim 1, wherein the amount of the group IIIA metal is in the range from 0.5 to 2% by weight based on the total weight of the catalyst.

9. The catalyst according to claim 1, wherein the group IIIA metal is gallium (Ga).

10. The catalyst according to claim 1, wherein at least 1 transition metal further comprises the group IVB transition metal.

11. The catalyst according to claim 10, wherein the amount of the group IVB transition metal is in the range from 0.1 to 10% by weight based on the total weight of the catalyst.

12. The catalyst according to claim 11, wherein the amount of the group IVB transition metal is in the range from 3 to 5% by weight based on the total weight of the catalyst.

13. The catalyst according to claim 10, wherein the group IVB transition metal is titanium (Ti).

14. The catalyst according to claim 1, wherein step b) and step d) are performed using the microwave at the power in the range from 600 to 900 watts.

15. The catalyst according to claim 14, wherein step b) and step d) are performed using the microwave at the power of 800 watts.

16. The catalyst according to claim 1, wherein step e) is performed at the temperature in a range from 400 to 600° C.

17. The catalyst according to claim 16, wherein step e) is performed at the temperature in the range from 500 to 600° C.

18. The catalyst according to claim 1, wherein the calcination time of step e) is from 3 to 6 hours.

19. The catalyst according to claim 1, wherein alkanes are pentane.

20. A process of aromatics preparation from aromatization of alkanes comprising:
  a) treating the catalyst according to claim 1 with gas comprising hydrogen gas at a temperature in a range from 200 to 650° C.; and
  b) contacting alkanes with the catalyst obtained from step a) at the temperature in the range from 400 to 800° C.

21. The process of aromatics preparation according to claim 20, wherein step a) is performed at the temperature in the range from 400 to 600° C.

22. The process of aromatics preparation according to claim 20, wherein step b) is performed at the temperature in the range from 500 to 600° C.

23. The process of aromatics preparation according to claim 20, wherein alkanes are pentane.

24. A process of catalyst preparation for aromatization of alkanes having 4 to 7 carbon atoms comprising:
  a) contacting a zeolite with a solution comprising at least 1 transition metal salt from group VIII transition metal to form a first mixture, wherein the group VIII transition metal is in a range of 0.1 to 2% by weight based on the total weight of the catalyst;
  b) treating and drying the first mixture obtained from step a) with a microwave at a power in a range from 400 to 1,000 watts to form a first dried mixture;
  c) contacting the first dried mixture obtained from step b) with a solution comprising at least 1 group IIIA metal salt to form a second mixture, wherein the group IIIA metal is in a range of 0.1 to 5% by weight based on the total weight of the catalyst;
  d) treating and drying the second mixture obtained from step c) with a microwave at a power in a range from 400 to 1,000 watts to form a second dried mixture; and
  e) calcining the second dried mixture obtained from step d) at a temperature less than or equal to 650° C.

25. The process of catalyst preparation according to claim 24, wherein the amount of the group VIII transition metal is in the range from 0.5 to 1% by weight based on the total weight of the catalyst.

26. The process of catalyst preparation according to claim 24, wherein the group VIII transition metal is platinum (Pt).

27. The process of catalyst preparation according to claim 24, wherein the amount of the group IIIA metal is in the range from 0.5 to 2% by weight based on the total weight of the catalyst.

28. The process of catalyst preparation according to claim 24, wherein the group IIIA metal is gallium (Ga).

29. The process of catalyst preparation according to claim 24, wherein the solution comprising at least 1 transition metal salt in step a) further comprises at least 1 transition metal salt from group IVB transition metal.

30. The process of catalyst preparation according to claim 29, wherein the amount of the group IVB transition metal is in the range from 0.1 to 10% by weight based on the total weight of the catalyst.

31. The process of catalyst preparation according to claim 30, wherein the amount of the group IVB transition metal is in the range from 3 to 5% by weight based on the total weight of the catalyst.

32. The process of catalyst preparation according to claim 29, wherein the group IVB transition metal is titanium (Ti).

33. The process of catalyst preparation according to claim 24, wherein the zeolite is selected from ZSM-5, ZSM-11, or a mixture thereof.

34. The process of catalyst preparation according to claim 33, wherein the zeolite is ZSM-5.

35. The process of catalyst preparation according to claim 24, wherein said zeolite has a mole ratio of silica to alumina in a range from 15 to 40.

36. The process of catalyst preparation according to claim 35, wherein said zeolite has the mole ratio of silica to alumina in the range from 20 to 30.

37. The process of catalyst preparation according to claim 24, wherein step b) and step d) are performed using the microwave at the power in the range from 600 to 900 watts.

38. The process of catalyst preparation according to claim 37, wherein step b) and step d) are performed using the microwave at the power of 800 watts.

39. The process of catalyst preparation according to claim 24, wherein step e) is performed at the temperature in the range from 400 to 600° C.

40. The process of catalyst preparation according to claim 39, wherein step e) is performed at the temperature in the range from 500 to 600° C.

41. The process of catalyst preparation according to claim 24, wherein the calcination time of step e) is from 3 to 6 hours.

42. The process of catalyst preparation according to claim 24, wherein alkanes are pentane.

* * * * *